United States Patent [19]
Eaton et al.

[11] Patent Number: 5,312,413
[45] Date of Patent: *May 17, 1994

[54] INSTRUMENTATION FOR OPHTHALMIC SURGERY AND METHOD OF USING THE SAME

[76] Inventors: Alexander M. Eaton, 910 Constitution Dr., Durham, N.C. 27705; Jaime Santamaria, 73 Water St., Perth Amboy, N.J. 08861

[*] Notice: The portion of the term of this patent subsequent to Aug. 10, 2010 has been disclaimed.

[21] Appl. No.: 834,142

[22] Filed: Feb. 10, 1992

Related U.S. Application Data

[63] Continuation-in-part of Ser. No. 731,444, Jul. 17, 1991, abandoned.

[51] Int. Cl.$^5$ .............................................. A61B 17/00
[52] U.S. Cl. ..................................... 606/107; 30/151; 606/167; 606/172
[58] Field of Search ............... 606/107, 108, 109, 110, 606/166, 167, 168, 169, 170, 171, 172, 173; 128/10, 11; 30/151

[56] References Cited

U.S. PATENT DOCUMENTS

| | | | |
|---|---|---|---|
| 1,242,415 | 10/1917 | Benson | 30/151 |
| 2,288,555 | 6/1942 | St. Jacques | 30/151 |
| 2,521,161 | 9/1950 | Grover | 606/167 |
| 4,494,542 | 1/1985 | Lee | 606/167 X |
| 4,569,133 | 2/1986 | Schmidt | 606/172 |
| 4,576,164 | 3/1986 | Richeson | 606/167 |
| 4,955,894 | 9/1990 | Herman | 606/167 |

FOREIGN PATENT DOCUMENTS

1533669  12/1989  U.S.S.R. ............... 606/128

*Primary Examiner*—Peter A. Aschenbrenner
*Attorney, Agent, or Firm*—Hopgood, Calimafde, Kalil, Blaustein & Judlowe

[57] ABSTRACT

For protection of the otherwise sharp protruding end of a given instrument for use in ophthalmic or other surgery, as when the instrument is to be used only after it has traversed the major part of a scleral tunnel, a shiftable guard or shield is manipulable after it has served its function of avoiding damage to hemorrhageable tissues adjacent tunnel-wall tissue, thereby exposing the sharp end only after safely passing the hemorrhageable region. Various embodiments are described.

53 Claims, 5 Drawing Sheets

INSTRUMENTATION FOR OPHTHALMIC SURGERY AND METHOD OF USING THE SAME

RELATED MATTERS

This application is a continuation-in-part of our copending application, Ser. No. 731,444, filed Jul. 17, 1991 now abandoned. The filing of said copending application was preceded by Disclosure Document No. 279382, dated Apr. 11, 1991 and filed Apr. 16, 1991 in the U.S. Patent and Trademark Office.

BACKGROUND OF THE INVENTION

The invention relates to instrumentation and techniques for ophthalmic surgery, particularly although not necessarily as the same pertains to cataract surgery.

Surgically induced astigmatism and inflammation limit the rate and the extent of visual rehabilitation following cataract surgery. To reduce the extent of these surgically induced limitations on visual rehabilitation, a number of new advances in surgical techniques have been developed. In particular, the advent of phacoemulsification in combination with long scleral-tunnel incisions has greatly reduced surgically induced astigmatism and inflammation, in addition to reducing the post-operative time necessary for the restoration of vision. Illustration and discussion of such techniques will be found in the book, "Small-Incision Cataract Surgery", edited by Drs. James P. Gills and Donald R. Sanders, published 1990 by SLACK Incorporated, Thorofare, N.J.

Despite these advances in technique, the performance of cataract surgery through a scleral-tunnel incision is technically difficult and may result in serious complications. One of the greatest difficulties is that of advancing instruments, such as surgical knives or intraocular lenses, through the scleral-tunnel incision without getting them caught on a part of the scleral tunnel. Inadvertent capture of a knife in the sclera can result in serious complications, such as the formation of false passageways, hemorrhage, or penetration into the retina and vitreous cavity.

Another dificulty arises from corneal folds and/or deformation of the eye, as can be induced by a straight instrument advanced through a scleral-tunnel incision. Typically, this difficulty results from incompatability of a straight instrument with the native curve of a scleral tunnel, and the need to angularly manipulate the instrument, from a direction which faces the cornea upon exit from the incision, to a direction which faces the cataractous lens. The combined effect of these factors interferes with the surgeon's visualization of the cataract during its removal, and can lead to complications such as corneal-endothelial injury, disruption of the posterior-lens capsule, and increased vitreous pressure.

BRIEF STATEMENT OF THE INVENTION

It is an object of the invention to provide improved instrumentation and methods which will enable ophthalmic surgery of the character indicated, with substantially reduced risk of complications and difficulties noted above.

A specific object is to provide an instrument guard or sheath which will allow the surgeon to advance a selected one of a variety of instruments to a desired location in and via a scleral-tunnel incision without risk of the instrument catching on wall tissue of the incision.

Another specific object is to provide an improved ophthalmic-instrument configuration which will inherently reduce the incidence of corneal-fold development and ocular deformation that are induced by current instrument designs.

The invention achieves these objects by provision of a guard or sheath for protection of the otherwise sharp protruding end of a given instrument for ophthalmic surgery, the guard or sheath being manipulable after serving its protective function in the course of scleral-tunnel insertion. The manipulation involves selective retraction of the guard or sheath so as to expose the operative end of the instrument for performance of its surgical function, once the scleral tunnel has been safely negotiated. After the instrument function has been performed, the guard or sheath may if desired be further manipulable to resume its protective function, thus enabling safe withdrawal of the instrument via the tunnel. Various configurations and arrangements are described.

DETAILED DESCRIPTION

Preferred and modified embodiments of the invention will be described in detail, in conjunction with the accompanying drawings. In said drawings:

FIG. 4b is a view similar to FIG. 3d, for the knife of FIG. 4a;

Figure 1:
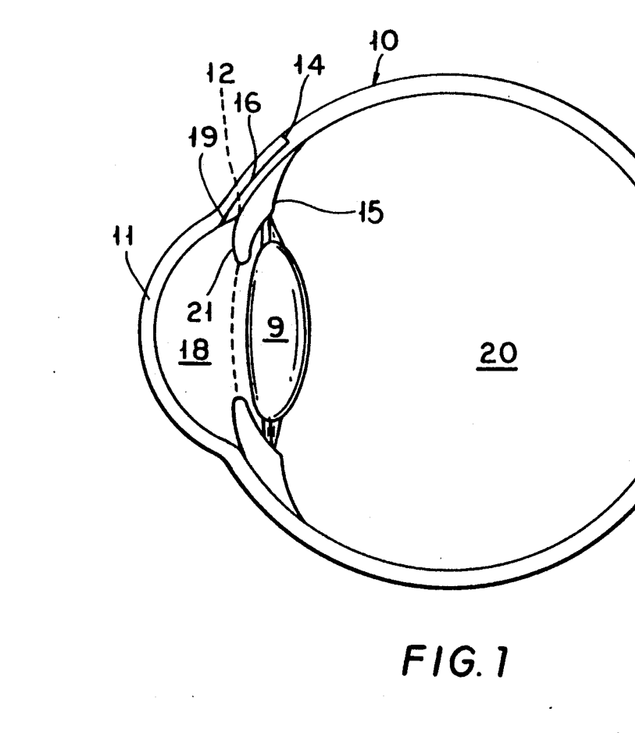
FIG. 1 is an enlarged cross-sectional view of an eye with dilated iris, and showing the path of a typical scleral tunnel via which instrumentation of the invention is to be introduced and manipulated, the conjuntiva being omitted in FIG. 1 for purposes of simplification.

The protective feature of the invention will be illustratively described in connection with a so-called phacoknife, which is the surgical tool used to complete the scleral-tunnelling procedure, for direct access into the anterior chamber. This knife alone, that is, without the protective feature of the invention may suitably be a commercially available product of Rudolph Beaver, Inc., Waltham, Mass., as for example Beaver Item 5522, which is characterized by a somewhat diamond-shaped, thin flat blade 3.2-mm wide, and at 45° divergence from the longitudinal axis, with two convergent blade edges of extreme sharpness; similarly illustrative is the angled 3.2-mm Alcon Ophthalmic Slit Knife, available from Alcon Surgical, Inc., Fort Worth, Tex. But first, it is well to review, in connection with FIGS. 1 to 3, the context of surgical procedures preceding use of the phacoknife. FIG. 1 depicts the section of an eye having a cataractous (crystaline) lens 9 to be surgically accessed in a scleral-tunnel procedure, through localized adjacent regions of the sclera 10, of the cornea 11 and of the juncture 12 of clear cornea with the sclera. Conjunctiva has been omitted from FIG. 1 for purposes of simplification, but it will be understood from the plan of the frontal-aspect view of FIG. 2 that an arcuate cut 13 is first made locally through the conjunctiva, to provide surgical access to and for an initial tunnelling cut 14. The scleral-tunnel incision follows the initial inward or vertical cut 14 to approximately half scleral thickness, illustratively using a standard 15° angled knife. This cut 14 may be of limited arc about the central axis of the eye but is shown with an inverted-V entering course. This initial cut 14 is preferably posterior to the ciliary body 15, for purposes of enabling stitchless completion of the surgery.

Figure 2:
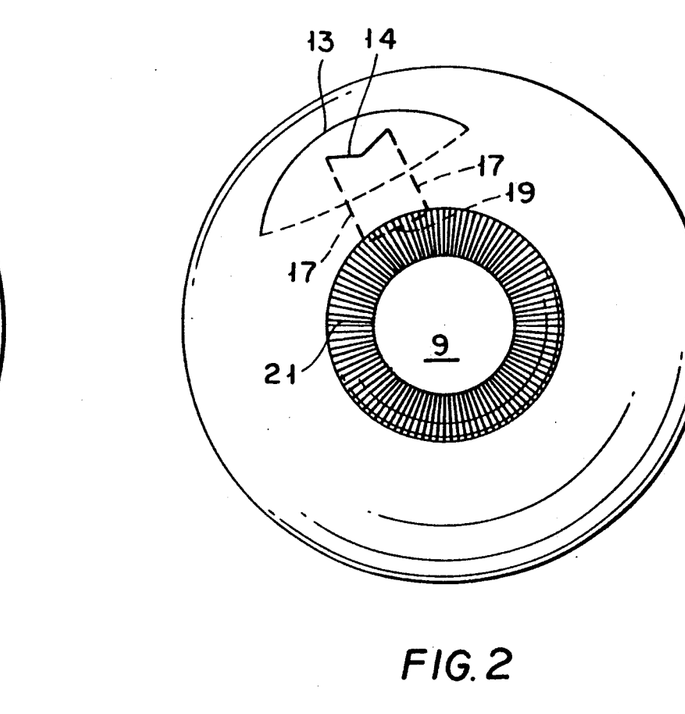
FIG. 2 is a simplified frontal-aspect view of the eye of FIG. 1, wherein a conjunctival incision is schematically shown, for access to the scleral tunnel of FIG. 1.
Figure 3A:
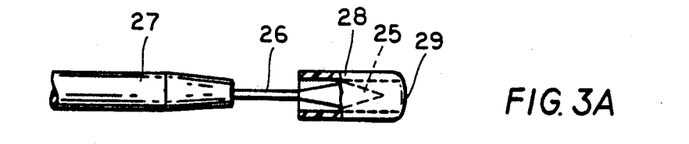
FIG. 3a is a fragmentary plan view of a phacoknife, with a protective device of the invention in protective position, and partly broken-away and in section.
Figure 3B:
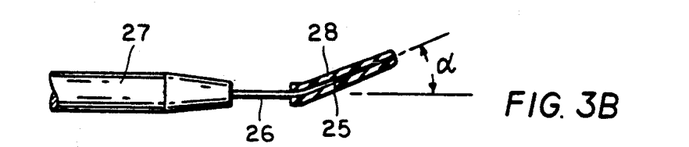
FIG. 3b is a view in side elevation of the knife of FIG. 3a with the protective device in section.
Figure 3C:
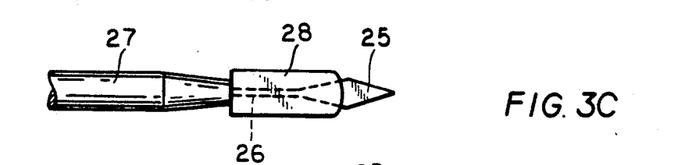
FIG. 3c is a view similar to FIG. 3a, with protective device in retracted position.
Figure 3D:
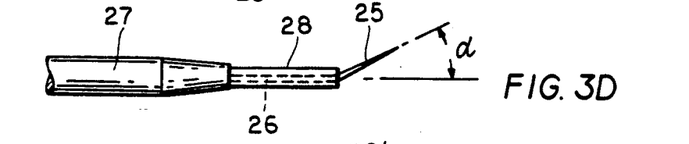
FIG. 3d is a side elevation, from the aspect of FIG. 3b and with the protective device in retracted position.

The next phase of scleral-tunnel formation is illustratively performed with a round-tip blade that is suitably flat, angled and sharpened to 260° of its circular extent; this blade is manipulated to develop the curved profile 16, of width shown between dashed lines 17 in FIG. 2, and to a location forward of juncture 12 and therefore in short overlap with the anterior chamber 18.

The third and last phase of scleral-tunnel formation involves use of a phacoknife to develop the vertical cut 19 at the anterior margin of the curved tunnel cut 16. But the phacoknife is so sharp and pointed that great skill is required to have its blade follow the course of the tunnel and to position and maneuver the same to achieve the vertical cut 19, without catching the pointed end on the tunnel wall. If the phacoknife catches the wall early and at high incidence, a penetration of the vitreous cavity 20 is likely; or if the knife catches the wall at lesser incidence but with penetration of the ciliary body 15, a severe hemorrhage is likely; or if the knife catches the wall further anterior to the point of tunnel entry, there may not only be a hemorrhage of the ciliary body but also damage to the iris 21; or if the pointed end of the phacoknife catches the other wall of the tunnel, a so-called "buttonhole" may be formed in the scleral pocket.

To avoid or at least to materially reduce the occurrence of such damaging consequences, the invention provides for blade protection, rendering the same so effectively blunt as to pose virtually no chance of catching an undesired tunnel or other surface, unless and until the blade has been maneuvered to the region in which it is to be surgically used. First and second embodiments of basically simple protected blade combinations are shown for the case of different phacoknives, in FIGS. 3 (a to d) and 4 (a and b), respectively.

In the structure of FIGS. 3a to 3d, a narrow, sharp-edged phacoknife element 25 is inclined at angle α to the central axis of its mounting stem 26 and elongate handle 27. A preformed sheath or sleeve 28, as of relatively pliable plastic or silicone rubber, surrounds the sharpened region of the knife blade 25, when in the protection position shown in FIGS. 3a and 3b; preferably, the material of sheath 28 is of sufficiently optically clear nature to allow visualization of the knife within the sheath. The distal end 29 of sheath 28 is rounded, for blunted insertional passage of the thus-guarded blade 25 along the curved course of tunnel 16, described in connection with FIGS. 1 and 2. Upon abutment with the anterior end of tunnel 16, a forceps grasp of the posterior end of sheath 28 is sufficient for selective manual retraction of the sheath to or short of the position of FIGS. 3c and 3d, thus exposing the sharp pointed end of blade 25 where needed for making the final vertical cut 19 into the anterior chamber 18, and at a location that is safely remote from any chance of hemorrhaging penetration of the ciliary body 15.

The sheath 28 may be a preformed cup that is flattened for frictional engagement to the flat surfaces of blade 25, i.e., with the blunt end 29 closed and subject to pierced opening by blade 25, as the forceps are drawn to retract the sheath and operatively expose the blade. But we prefer that the blunt end 29 shall not be closed, thus providing no 20 occasion for any degradation of the cutting edges of blade 25. Having performed the surgical procedure involved in completing tunnel access to the anterior chamber, the surgeon can assure similar protection against inadvertent blade damage to any part of the tunnel wall, simply by forceps grasp of the sheath to advance the same into its former blade-guarding position, before making a manipulated retraction of the thus-guarded blade. In the course of the described insertion and withdrawal phases with a sufficiently blunt-edged sheath 28, it will be appreciated that not only is there no danger of inadvertent tunnel-wall penetration, but the blunt nature of the sheath profile aids in virtually self-piloting entry into and withdrawal of the bladed tool from the freshly cut tunnel passage.

Figure 4A:
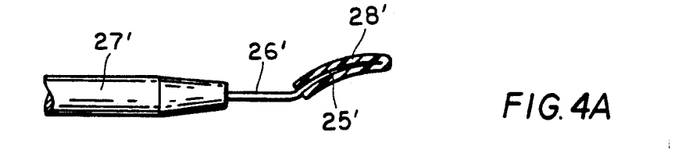
FIG. 4a is a view similar to FIG. 3b, for a modified knife of the invention.
Figure 4B:
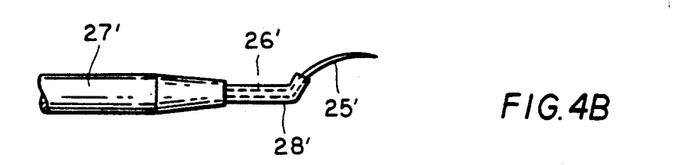

The embodiment of FIGS. 4a and 4b will be recognized for its similarities to the embodiment of FIGS. 3a to 3d. For this reason the same reference numbers have been adopted for corresponding parts in FIG. 4, with primed notation. The point of difference is that the flat blade 25 of FIG. 3 is an arcuately curved blade 25' in FIG. 4, the arcuate curvature being selected for substantial conformance with the curved segment 16 of the tunnel path. The sheath 28' in FIG. 4 may be as described for FIG. 3, relying on its inherent pliability to adapt to the curvature of blade 25' Forceps retraction and replacement of sheath 28' in FIG. 4 is as described for FIG. 3.

In the embodiment of FIGS. 5 to 8, an illustrative knife blade 30 is provided with blunt-nosed sheath protection 31 which is remotely actuable in the course of a given surgical procedure and which therefore does not need forceps or other actuating assistance; sheath 31 may be of a material as discussed for sheath 28 in FIG. 3. Specifically, an annular actuator or ring 32, as of injection-molded ABS or other suitable plastic material, is slidable along the cylindrical body portion of the manipulating handle 33 for blade 30 and is connected to a tie element 34 forming part of sheath 31. As shown, the body of handle 33 is formed with an elongate cap-groove 35, of width and depth to locate the tie element 34, to the point of its snap-lock engagement to a local recess or opening 36 in ring 32. An integrally formed inward lug formation 37 of ring 32 has keyed engagement in groove 35, and an outward lug formation 38 at the actuating end of tie element 34 has a ramp contour to transiently stress a bridge portion 39 of ring 32 in the course of inserted assembly, prior to snap-locking engagement to ring 32 at opening 36.

Figure 5:
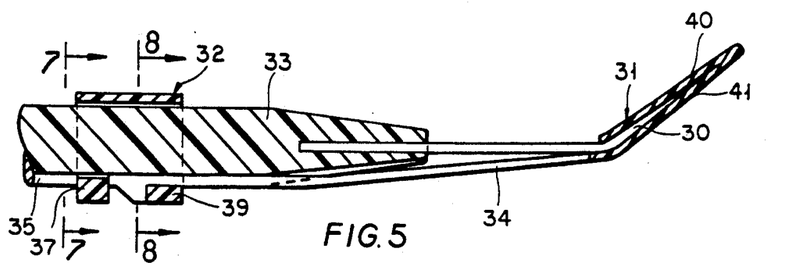
FIG. 5 is a fragmentary longitudinal sectional view of another embodiment of the invention.
Figure 6:
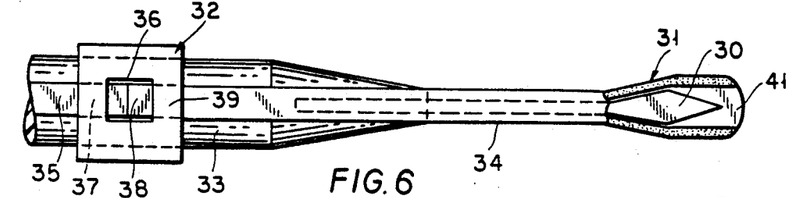
FIG. 6 is a view as seen from the underside of the embodiment of FIG. 5.
Figure 7:
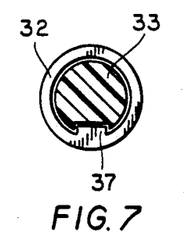
FIG. 7 is a sectional view, taken at 7—7 in FIG. 5.
Figure 8:
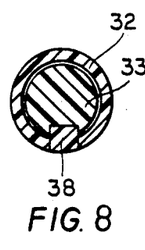
FIG. 8 is a sectional view, taken at 8—8 in FIG. 5.

The sheath 31 may comprise a sandwich of edge-welded upper and lower halves 40, 41 of plastic sheet material having the peripheral contour seen in FIG. 6, wherein stippled margins indicate the course of the weldments which complete the sheath. Preferably, as shown, the lower sheath half 41 is an integral formation with tie element 34, and the internal passage of sheath 31 is open for the full width of blade 30, for unimpeded blade passage through the rounded blunt end, in the course of sheath retraction via a finger-operated sliding retraction of ring 32. Whether sheath 31 is the result of assembling separate halves 40, 41 or is the result of folding a single blank to lap and register two fold-connected halves 40, 41, the preference is indicated to edge-weld the same along stippled margins, using known ultrasonic-weld techniques. If made from plastic sheet material, it will be understood that the ramped lug 38 which has snap-locking engagement to ring 32 may be a product of ultrasonic forming to shape; alternatively, the entire part, comprising the lower half 41 (with or without the upper half 40) plus tie piece 34 and its snap-locking end formation 38, may be a single injection-molded product.

Figure 9:
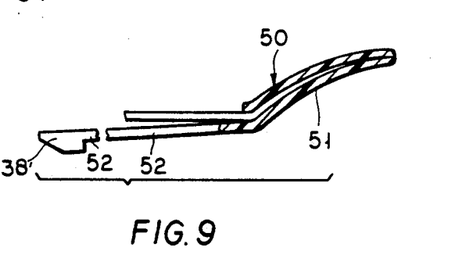
FIG. 9 is a fragmentary diagram, similar to part of FIG. 5, to show a modification.

It will be appreciated that the described structure of FIGS. 5 to 8 is applicable to a variety of surgical-implement configurations, particularly where the same handle (33) design serves for mounting a variety of different knife or other-tool shapes. The handle 33 and its elongate groove 35 are readily assembled to ring 32, with the blade end of the tool. The sheath 31, sized and shaped in optimum accommodation of the blade or other instrument it is to serve, is assembled to the blade, and its halves 40, 41 then welded to each other, with tie element 34 located in groove 35 and with lug 38 snap-engaged to ring 32 at opening 36. The blunt end of the sheath pilots readily along the tunnel alignment 16; and when the surgeon determines that the tip of blade 30 is sufficiently advanced for safe surgical entry (19) into the anterior chamber 18, he need not even change his hold of handle 33, in that a single-finger retracting actuation of ring 32 (as with the thumb of the same hand) will enable his total manipulative control of the location which he selects for blade-tip exposure beyond the sheath, to make the cut 19. Having safely entered the anterior chamber, the phacoknife is directly viewable. And when the knife has served its purposes, knife removal via the scleral tunnel is safely accomplished even if sheath 31 is not advanced to envelop the blade, in that in any such tool removal, the sheath 31 effectively pilots the blade in the tunnel throughout the course of tool withdrawal. As indicated generally above, the retractable-sheath concept of the invention is applicable to a wide range of surgical tools, and certainly to those for use in ophthalmic surgery. For example, FIG. 9 illustrates application of a retractable sheath 50 to an arcuate phacoknife 51, wherein an integral tie element 52 has a snap-locking formation 38' for engagement to an actuating ring, as at 32 in FIG. 5.

Figure 10:
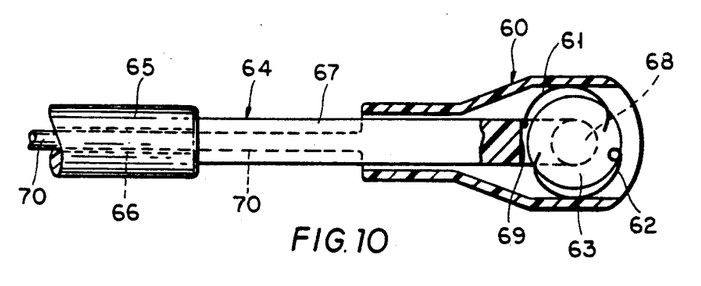
FIG. 10 is a fragmentary diagram, generally similar to part of FIG. 6, but showing another embodiment of the invention.

Also, by way of example, having completed the capsulorhexis by forceps removal of capsular-bag tissue, and having removed cataractous-lens tissue, by acoustic phacoemulsification or otherwise, the capsular bag will have been prepared for intraocular-lens implantation. And if the intraocular lens is inserted in sheathed condition, opposing haptics may be contained within the sheath until such time as it is presented to the open capsulary bag, all without danger of exposing a haptic to any possible inadvertent snagging engagement to the corneal endothelium or otherwise within the anterior chamber. Specifically, FIG. 10 shows use of a suitable sheath 60, analogous to sheaths described for knife blades, except that in FIG. 10, the sheath safely confines the compliantly stressed haptics 61, 62 of an intraocular lens 63. An insertion tool 64 has a cylindrical handle portion 65 with an elongate tie-guide groove 66, and a stem portion 67 is bifurcated at its distal end with circular pads 68 (which register in the view of FIG. 10) for gently protected locating support of lens 63, while a crotch 69 at the point of bifurcation provides a limit stop, in further stabilization of lens 63. An integrally formed tie element 70 extends for longitudinal guidance in groove 66 and will be understood to be provided with a lug formation (not shown) for preferably snap-lock engagement to a slidable actuating ring (also not shown, but analogous to ring 32 in FIG. 5).

In operation, the lens-loaded tool 64 is manipulated to the point of entry into a prepared open capsulary bag, whereupon sheath 60 is carefully actuated for retraction, making sure that the diametrically opposed points of haptic engagement to the sheath are well within the volumetric enclosure of the capsulary bag, thus assuring that when the haptics clear the sheath and are released for resilient outward expansion, they will make their own lens-stabilizing contact with opposed inner walls of the bag. This contact will be understood to be more than sufficiently firm than is needed for release of pad (68) engagement with lens 63, so that the tool 64 and its sheath may be retracted, leaving the lens implant with emplaced haptics.

Figure 11:
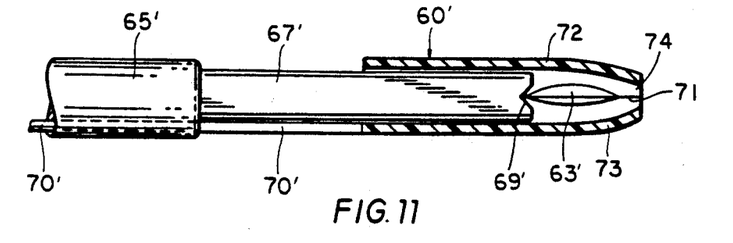
FIG. 11 is a view, partly in side elevation and partly in section of a slightly modified version of the device of FIG. 10, the aspect of view being 90° rotated about the longitudinal axis, with respect to the aspect of view in FIG. 10.

In the arrangement of FIG. 11, the lens 63' derives stabilizing support from stem 67' only by way of a transverse groove or crotch formation 69' at the distal tip end of the stem. Frictional retention of the lens is by way of stressed confinement of the two haptics (not shown in FIG. 11) in the alignment 71 afforded by pinched convergence of the registered panel halves of the sheath, adjacent the region of edge-welding these halves. Manipulation and controlled release of the intra-ocular lens unit of FIG. 11 is as described in connection with FIG. 10.

FIG. 11 will be understood to serve the further purpose of illustrating the blunt-nosed nature of sheaths 60 and 60', in that the separate panel halves 72, 73 converge distally beyond the end of the stem, to define a flattened mouth 74 for exit passage of the lens assembly when the sheath is actuated for retraction, it being recalled that the material of the panel halves 72, 73 is compliant and therefore expandable at mouth 74 in the course of sheath retraction over the stem.

Figures 12, 13:
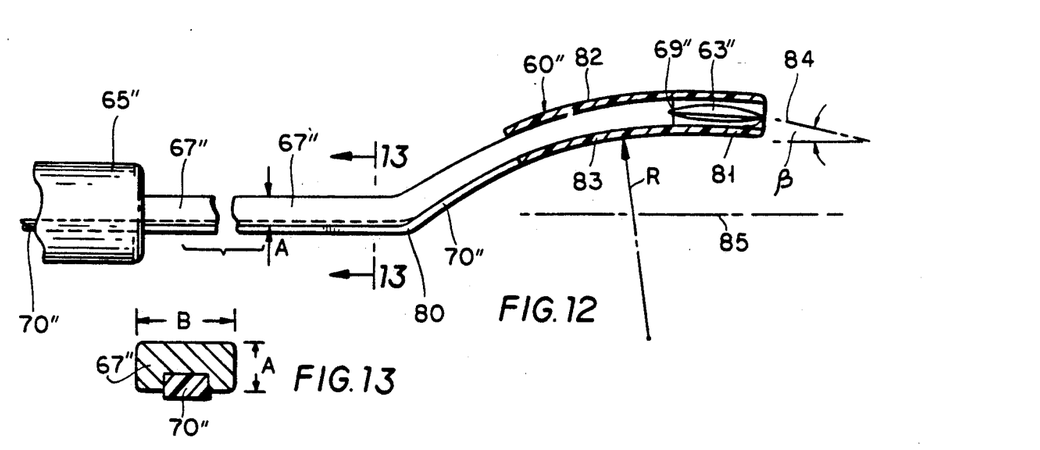
FIG. 12 is a view similar to FIG. 11, for another modification.
FIG. 13 is an enlarged section, taken at 13—13 in FIG. 12.

The lens-insertion device of FIGS. 12 and 13 will be recognized for its similarity to those of FIGS. 10 and 11, and therefore corresponding parts are given the same reference numbers, with double-prime notation. Briefly, the stem 67" of FIG. 12 is seen to include an angularly offsetting bend at 80, and the elongate course of the angularly offset portion of the stem is generally arcuate, with a curvature of radius R which is preferably at least no greater than the curvature of the scleral tunnel (i.e., of the sclera). As also seen by reference to FIG. 13, the section of stem 67" is preferably relatively thin in its dimension A, compared to its width B, and a shallow groove in at least the straight proximal region of the stem provides guided retention of the tie element 70". Further, the region in which sheath 60" projects beyond the distal end of stem 67", is formed as a continuation of the arcuate curvature of the stem and with a pair of haptic-locating creases, e.g., at 81 between welded edges of halves 82, 83, such that lens 63" is poised for ultimate release on an alignment 84 which is inclined slightly, at an angle β, below parallelism with the geometrical projection 85 of the axis of the proximal end of stem 67". The latter feature will be seen as a material aid to lens and haptic insertion into and safe release within an open capsulary bag.

Figure 14:
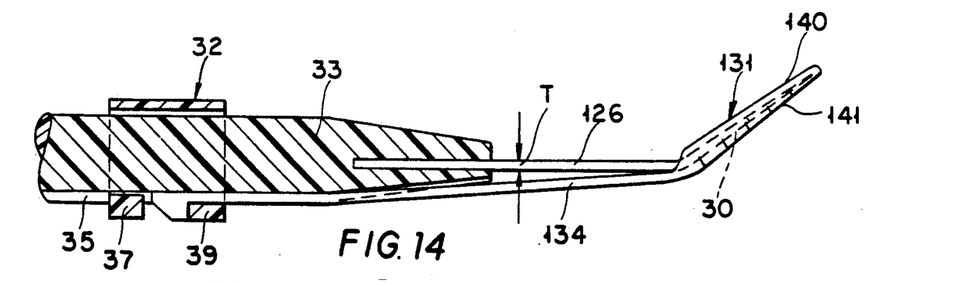
FIG. 14 is a view similar to FIG. 5 to show a modification.
Figure 15:
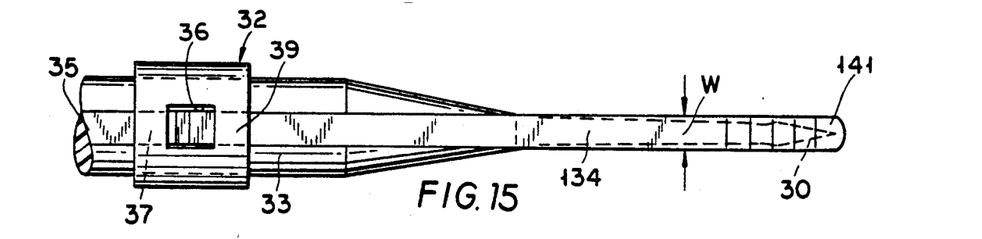
FIG. 15 is a view as seen from the underside of FIG. 14.
Figures 16, 17, 18, 19, 20, 21, 22:
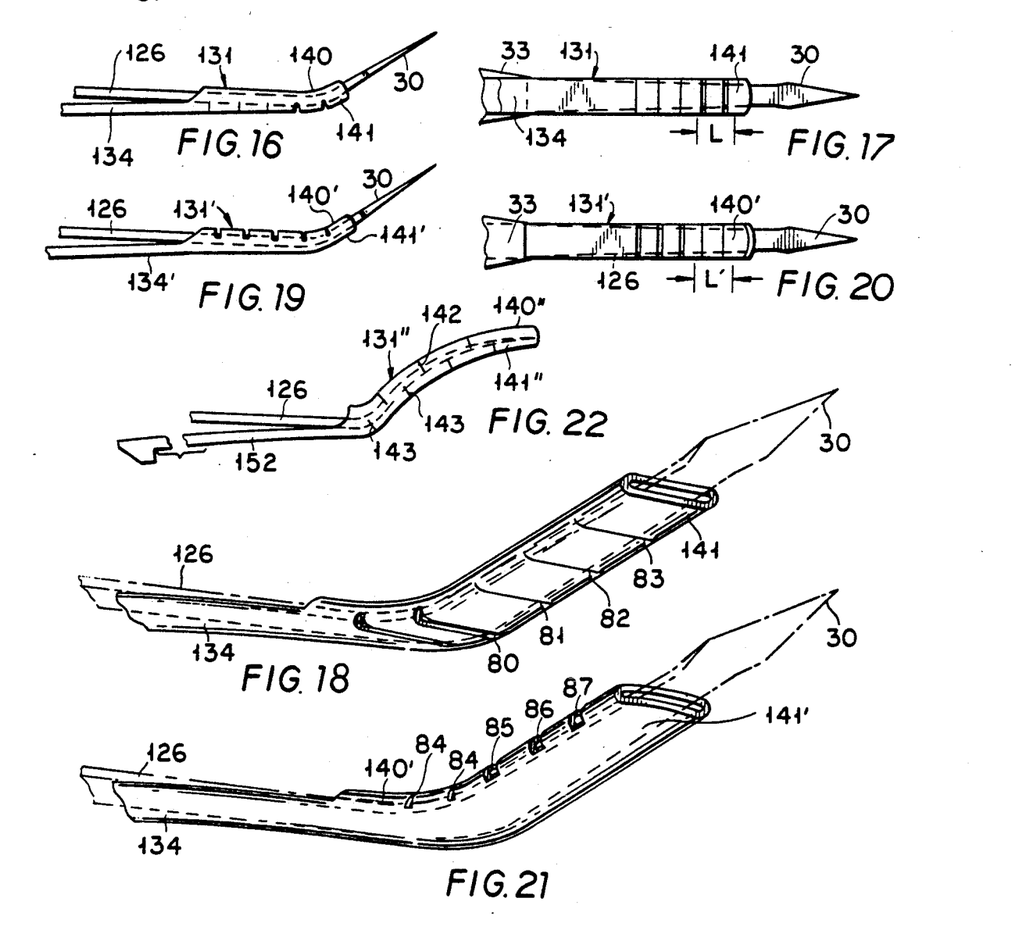
FIGS. 16 and 17 are, respectively, side and underside views of operative parts of the embodiment of FIGS. 14 and 15, for a different relation of the involved parts.
FIGS. 18 and 19 are, respectively, side and plan views of operative parts of a modification of the embodiment of FIGS. 14 and 15.
FIG. 20 is an enlarged fragmentary view in perspective of the parts relation of FIGS. 16 and 17.
FIG. 21 is an enlarged fragmentary view in perspective of the parts relation of FIGS. 19 and 20.
FIG. 22 is a fragmentary view in side elevation for another embodiment.

The embodiment of FIGS. 14 and 15 closely resembles the embodiment of FIGS. 5 and 6, and therefore previously identified parts carry the same reference numbers and need not be further described. One point of difference is that the stem 126 in FIGS. 14 and 15 is of rectangular section, wherein the width W is greater than the thickness T. The tie element 134 is also of rectangular section and has substantial lap of the width of stem 126, on the convex side of the bend which defines the direction of angular offset of the sharpened blade 30. The other and more important point of difference is that one of the panels, specifically panel 141, is transversely slitted at longitudinally spaced intervals. To have thus slitted panel 141 will be seen to enable panel 141 to incrementally stretch locally and with ease, in the course of sheath 131 retracton and as the sheath locally negotiates the bend on its way to ultimate retention along the stem, within the region from the bend to handle 33. Such local stretch action is seen in FIGS. 16 and 17 as a short local region L wherein a few consecutive slits of panel 141 elastically open to slots. In the enlarged perspective of FIG. 18, slit 80 of the lower panel 141 is seen to have transiently enlarged to a slot while its adjacent slits 81 are substantially in their undeformed state.

FIGS. 19 and 20 illustrate, in the manner of FIGS. 16 and 17, an alternative construction wherein the lower panel (141') of sheath 131' is not slitted but, rather, the upper panel 140' is transversely slotted at longitudinally spaced locations. As long as the sheath 131' envelops a straight or less-curved region of stem 126 and/or blade 30, the slots are at maximum width, but upon retraction of the sheath, a succession of slots in the portion of the sheath where sheath 131' is negotiating the angular-offset bend will narrow in resilient local longitudinal shrinkage of the upper panel 140'. Such local shrink action is seen in FIGS. 18 and 19 and a short local region L' wherein a few consecutive slots of panel 140' are elastically compressed into slits. In the enlarged perspective of FIG. 19, slots 84 of panel 140' at the region of the bend of stem 126 are seen to have been resiliently compressed, while adjacent slots 85 to 88 remain in their unstressed full-width state.

FIG. 22 illustrates a further embodiment wherein the sheath 131" must readily adapt to a reverse curvature, in the course of retraction along the curved blade (151) of an arcuate phacoknife, at angular offset from its supporting stem 126, as in the case of FIG. 9. In FIG. 22, the stem 126 is again of rectangular section, and the sheath 131" has opposed panels 140", 141", each of which is transversely slitted at longitudinally spaced points, with the slits 142 of panel 140" in longitudinal interlace with the slits 143 of panel 141".

FIG. 22 may also be taken to illustrate the case in which the distal end of sheath 131" is initially closed and in which the phacoknife 151 has a sharp pointed distal end. In such case, initial retraction of the sheath causes the pointed end of the blade to cut through and open up the erstwhile closed distal end of the sheath, and in the course of the retracting sheath negotiating the reversed curvatures of the blade and its stem, each of the slitted panels 140", 141" affords maximum sheath stretch/shrink action as the arcuate-blade curvature and as the curvature of the angular offset bend regions are traversed.

In all pliable-sheath cases, it is preferred that the sheath be of low-friction plastic material, it being noted that thin Teflon (PTFE) tubing has been found to be highly satisfactory. Such tubing is first compressed to establish the flat opposed panels which have been described (at 40, 41; 50, 51), and the slits or slots described for panels of FIGS. 14 to 22 are cut or otherwise formed (e.g., 140, 141) across the full transverse extent of the applicable panel or panels.

Figure 23:
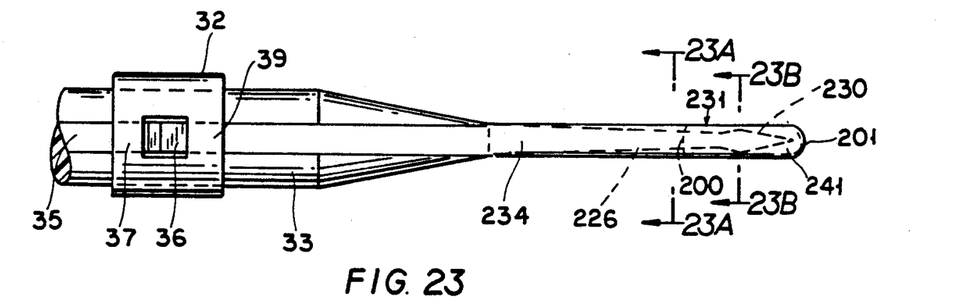
FIG. 23 is a view similar to FIG. 15 to show another embodiment.
Figure 23A:
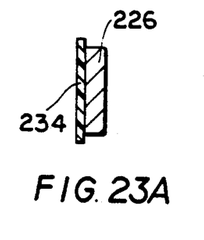
FIGS. 23a and 23b are enlarged sectional views, respectively taken at 23a—23a and at 23b—23b of FIG. 23.
Figure 24:
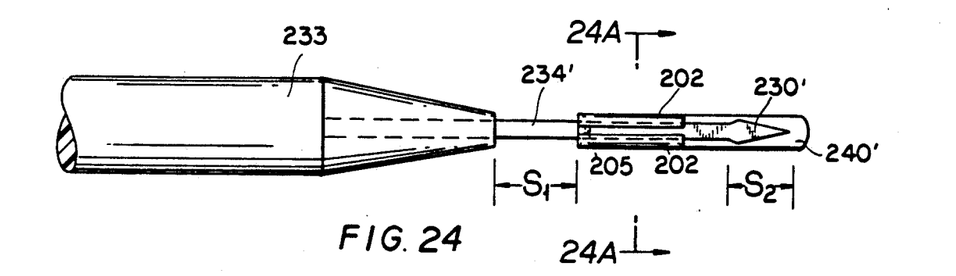
FIG. 24 is a view similar to FIG. 23, to show another embodiment.
Figure 25:
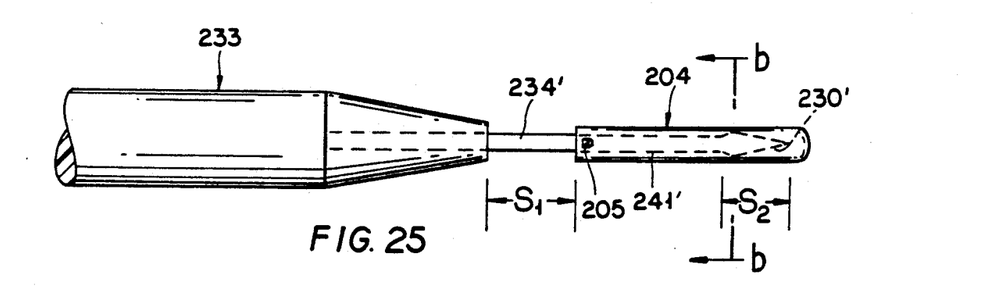
FIG. 25 is another view similar to FIG. 23, for still another embodiment.

FIGS. 23 to 25 are illustrative of sheathed surgical-knife configurations wherein the blade at the distal end of its integrally formed elongate stem is not at angular offset, so that flexibility is not needed to negotiate a bend, in the course of sheath retraction. The sheaths of these figures may therefore be of more rigid and therefore less-compliant material.

In FIG. 23, the knife blade 230 extends longitudinally beyond the distal end of its integrally formed elongate stem 226, and the proximal end of stem 226 is securely embedded in a handle 33, as in FIG. 15. The sheath 231 which is shown enveloping blade 230 comprises opposing panels 240/241 and extends from a proximal end 200 to a blunt distal end 201. A tie element 224 is an integral formation with panel 241 and has actuable connection to a slide ring 32 on handle 33. Light frictional retention of the blade-protecting position of sheath 231 may be incorporated in the engagement of ring 32 to handle 33, or at least some of the frictional retention may be provided by lightly squeezing contact of panels 240/241 with opposite surfaces of blade 230, as suggested in FIG. 23b. The material of sheath 231 and its tie element 234 may be of relatively thin non-pliant plastic or of relatively thin sheet metal.

Figure 24A:
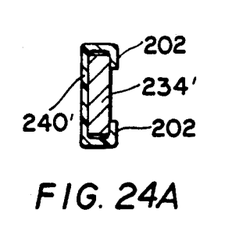
FIG. 24a is an enlarged sectional view, taken at 24a—24a of FIG. 24.

In FIG. 24, the handle 233 is shown only to provide a secure embedment base for a stem 234' which integrally carries a straight sharp blade 230' at its distal end. As seen in FIG. 24a, stem 234' is of constant rectangular section, and blade (230') protection is provided by a single sheath panel 240', of length to amply cover the full extent $S_2$ of blade 230'. As shown, the distal half of panel 240' rides one face of the rectangular section of the element 234', and the distal half of panel 240' is formed with stabilizing guide flanges 202 which lap outer edges of the other face of the section of element 234'. In the blade-protecting position shown in FIG. 24, a span $S_1$ exists between panel 240' and the distal end of handle 233'; this span $S_1$ exceeds the blade length $S_2$, so that in the retracted position of the sheath panel 240', the blade is fully exposed for surgical use.

The stretch panel 240' of FIG. 24 is suitably formed of thin relatively stiff material which may be metal or plastic. And the flanges 202 exhibit a degree of compliant connection to the part of panel 240' which fully engages the adjacent surface of the section of stem 234', thus permitting sufficient transient spreading of flanges 202 from each other, for snap-action assembly of the sheath panel 240' to its guiding stem 234'. At the same time, it will be understood that the compliant nature of sheath panel 240' enables an assembled panel 240' to lightly and frictionally load its flat distal end against one surface of the blade 230'. Also, at the same time, the overall elongation of panel 240' is such that its proximal end is accessible for direct manual, tweezer or other actuating engagement, so that by its nature the proximal end of panel 240' of FIG. 24 is its own actuating means.

The distal half of panel 240' will be understood to be either flat or slightly concave, for smooth conformity to the blade profile against which it lies, in the protecting position shown. This profile conformance alone, in conjunction with the lightly resilient loading of this distal half against the blade provides sufficient friction for retention of the blade-protecting relation. If the surgeon opts to discard the sheath panel 240', the blade-protecting function has already been performed, and it is a simple act of spreading the flanges 202, to enable removal of the sheath panel. Alternatively, the sheath panel can be actuated to retracted position after the blunt-nose end of the panel has enabled safe surgical passage through a surgically prepared tunnel incision.

Figure 23B:
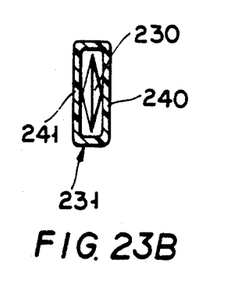

The embodiment of FIG. 24 differs from that of FIG. 24 in that its sheath 204 fully envelops blade 230' so that the blade/sheath relation at the section plane b—b of FIG. 25 is as depicted in FIG. 23b. Sheath 204 is elongate and is shown with a small lug 205 at its proximal end, it being indicated that lug 205 may be formed from one (241') of the opposed panels of sheet 204, e.g., struck outwardly from a small "horseshow" piercing of panel 241', thereby providing a means of manually actuating sheath 204 for retraction over the span $S_1$ to fully expose blade 230'. A similar lug, suggested at 205 in the single sheath panel of FIG. 24, may similarly serve actuating purposes for the embodiment of FIG. 24.

What is claimed is:

1. In combination, an elongate handle mounting a bladed surgical implement at the end of a longitudinal stem which offsets the implement beyond an end of the handle, said implement being at angular offset with respect to said stem, a sheath of pliant material having a through passage which envelops the implement, an elongate tie element connected to said sheath and extending to a point of longitudinally guided location at said handle, and said sheath having opposed closely spaced relatively wide panels with such frictional engagement to opposite surfaces of the blade of said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, one of said relatively wide panels being transversely slitted at longitudinally spaced locations, thereby facilitating sheath retraction from the blade of said implement and sheath negotiation of the angular offset which connects the implement to said stem.

2. The combination of claim 1, in which the longitudinal extent of said stem beyond said handle is approximately the length of said sheath.

3. The combination of claim 1, in which an actuating ring slidably guided by said handle is connected to said tie element.

4. The combination of claim 1, in which said stem is of flat generally rectangular section and is bent at its outer end to provide said angular offset.

5. The combination of claim 4, in which said tie element is also of generally rectangular section and is connected to the sheath panel which is guided around the convex side of the bend of said angular offset.

6. The combination of claim 5, in which said tie element is an integral formation of said sheath.

7. The combination of claim 5, in which said tie element is connected to the slitted panel, the other panel having no slits.

8. The combination of claim 1, in which each of said panels has longitudinally spaced transverse slits, the slits of one panel being in longitudinally spaced interlace with respect to slits of the other panel.

9. The combination of claim 5, in which said tie element is connected to the panel which is opposite the slitted panel.

10. The combination of claim 3, wherein said handle has a longitudinal groove and said ring includes an inward lug having keyed engagement in said groove.

11. The combination of claim 1, wherein said handle has a longitudinal groove in longitudinally guiding location of said tie element.

12. The combination of claim 10, wherein said ring and said tie element are separate pieces having snap-look engagement.

13. The combination of claim 1, in which the angularly offset elongate course of said implement is generally arcuate, and said sheath compliantly conforms to said course.

14. The combination of claim 13, in which the general arc of said course is in the direction of reducing angular deviation from the axis of said stem.

15. A phacoknife assembly, comprising an integrally formed sharp-pointed blade having opposed surfaces at angular offset from an elongate stem, an elongate handle mounting said stem at one longitudinal end, the exposed length of said stem being at least the length of the bladed angular offset, and a sheath in peripheral overlap of said blade and having opposed panels in compliantly engaged relation to said blade surfaces, said sheath being closed at its distal end for actuated piercing and through-passage of said blade upon actuated retraction of said sheath, and one of the panels of said sheath being transversely slitted at longitudinally spaced locations.

16. The phacoknife assembly of claim 15, wherein a tie element connected to the proximal end of one of the panels of said sheath extends to a location of longitudinally guided relation with said handle.

17. The phacoknife assembly of claim 16, wherein said stem is of rectangular section of width exceeding thickness and said angular offset is a bend of the thickness dimension of the section, said tie element having slidable engagement to the convex surface of said angular-offset bend.

18. In combination, an elongate handle mounting a bladed surgical implement at the end of a longitudinal stem which offsets the implement beyond an end of the handle, said implement being at angular offset with respect to said stem, a sheath of pliant material having a through passage which envelops the implement, actuating means accessible in the vicinity of said handle and connected to said sheath for selectively retracting said sheath from its position of enveloping the implement, and said sheath having opposed closely spaced relatively wide panels with such frictional engagement to opposite surfaces of the blade of said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, one of said relatively wide panels being transversely slitted at longitudinally spaced locations, thereby facilitating sheath retraction from the blade of said implement and sheath negotiation of the angular offset which connects the implement to said stem.

19. In combination, an elongate handle mounting a bladed surgical implement at the end of a longitudinal stem which offsets the implement beyond an end of the handle, said implement being at angular offset with respect to said stem, a sheath of pliant material having a through passage which envelops the implement, actuating means associated with the proximal end of said sheath for selectively retracting said sheath from its position of enveloping the implement, and said sheath having opposed closely spaced relatively wide panels with such frictional engagement to opposite surfaces of the blade of said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, one of said relatively wide panels being transversely slitted at longitudinally spaced locations, thereby facilitating sheath retraction from the blade of said implement and sheath negotiation of the angular offset which connects the implement to said stem.

20. In combination, an elongate handle mounting a bladed surgical implement at the end of a longitudinal stem which offsets the implement beyond an end of the handle, said implement being at angular offset with respect to said stem, a sheath of pliant material having a through passage which envelops the implement, an elongate tie element connected to said sheath and extending to a point of longitudinally guided location and frictional restraint at said handle, and said sheath having opposed closely spaced relatively wide panels adjacent opposite surfaces of the blade of said implement, said frictional restraint being sufficient to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, one of said relatively wide panels being transversely slitted at longitudinally spaced locations, thereby facilitating sheath retraction from the blade of said implement and sheath negotiation of the angular offset which connects the implement to said stem.

21. In combination, an elongate handle mounting a bladed surgical implement at the end of a longitudinal stem which longitudinally offsets the implement beyond an end of the handle, a sheath having a through passage which envelops the implement, an elongate tie element connected to said sheath and extending to a point of longitudinally guided location at said handle, and said sheath having opposed closely spaced relatively wide panels with such frictional engagement to opposite surfaces of the blade of said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said elongate tie element having longitudinally aligned and smoothly continuous connection to one to the exclusion of the other of said panels.

22. In combination, an elongate handle mounting a bladed surgical implement at the end of a longitudinal stem which longitudinally offsets the implement beyond an end of the handle, a sheath having a through passage which envelops the implement, actuating means accessible in the vicinity of said handle and connected to said sheath for selectively retracting said sheath from its position of enveloping the implement, and said sheath having opposed closely spaced relatively wide panels with such frictional engagement to opposite surfaces of the blade of said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said actuating means having longitudinally aligned and smoothly continuous connection to one to the exclusion of the other of said panels.

23. In combination, an elongate handle mounting a bladed surgical implement at the end of a longitudinal stem which longitudinally offsets the implement beyond an end of the handle, a sheath having a through passage which envelops the implement, actuating means associated with the proximal end of said sheath for selectively retracting said sheath from its position of enveloping the implement, and said sheath having opposed closely spaced relatively wide panels with such frictional engagement to opposite surfaces of the blade of said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said actuating means having longitudinally aligned and smoothly continuous connection to one to the exclusion of the other of said panels.

24. In combination, an elongate handle mounting a bladed surgical implement at the end of a longitudinal stem which longitudinally offsets the implement beyond an end of the handle, a sheath having a through passage which envelops the implement, an elongate tie element connected to said sheath and extending to a point of longitudinally guided and frictional restraint location at said handle, and said sheath having opposed closely spaced relatively wide panels adjacent opposite surfaces of the blade of said implement, said frictional restraint being sufficient to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said elongate tie element having longitudinally aligned and smoothly continuous connection to one to the exclusion of the other of said panels.

25. In combination, an elongate handle mounting a bladed surgical implement at the end of a longitudinal stem which longitudinally offsets the implement beyond an end of the handle, a sheath having a through passage which envelops the implement, means providing frictional restraint against sleeve displacement with respect to said stem and implement, actuating means associated with the proximal end of said sheath for selectively retracting said sheath from its position of enveloping the implement, and said sheath having opposed closely spaced relatively wide panels adjacent opposite surfaces of the blade of said implement, said frictional restraint being sufficient to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said actuating means having longitudinally aligned and smoothly continuous connection to one to the exclusion of the other of said panels.

26. In combination, an elongate handle mounting a bladed surgical implement at the end of a longitudinal stem which longitudinally offsets the implement beyond an end of the handle, a sheath member having a proximal end in longitudinally guided relation with said stem and having a distal-end panel in overlap of one to the exclusion of the other opposed surface of the blade of said implement, means associated with said sheath member for providing restraint against longitudinal displacement with respect to said stem and implement, said frictional restraint being sufficient to permit panel-lapping implement insertion along a surgically prepared tunnel, prior to retraction of said sheath member to thereby expose said implement for its part in a surgical procedure wherein the operative use of said implement is to occur only after panel-piloted insertional passage through at least a predetermined portion of the prepared tunnel.

27. The combination of claim 26, in which said proximal end comprises a single panel with lateral flanges which extend sufficiently around said stem for guided retention by said stem.

28. The combination of claim 27, in which at least one of said side flanges has laterally compliant connection to the proximal end of said sheath member, whereby to permit selective snap-locking assembly to and removal from guided engagement with said stem.

29. In combination with a surgical knife instrument, wherein an elongate handle mounts a surgical bladed implement at the end of a longitudinal stem which offsets the implement beyond an end of the handle, said bladed implement having a transverse section which has a maximum width that substantially exceeds the thickness of said section, a sheath of pliant material having a through passage which substantially conforms to said maximum-width section and which envelops the implement, said sheath having a blunt profile at its distal end, and said sheath having such frictional engagement with said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, and a rearwardly extending retraction element of pliant material connected to the proximal end of said sheath, whereby said retraction element provides flexible means of remotely actuated retraction of said sheath.

30. In combination with a surgical knife instrument, wherein an elongate handle mounts a surgical implement at the end of a longitudinal stem which offsets the implement beyond an end of the handle, a sheath of pliant material having a through passage which envelops the implement, said sheath having a blunt profile at its distal end, and said sheath having such frictional engagement with said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, and an elongate tie element connected to said sheath extending to a point of longitudinally guided location at said handle, whereby said tie element provides means of remote actuation of said sheath.

31. The combination of claim 30, in which the longitudinal extent of said stem beyond said handle is approximately the length of said sheath.

32. The combination of claim 30, in which an actuating ring slidably guided by said handle is connected to said the element.

33. The combination of claim 32, wherein said handle has a longitudinal groove and said ring includes an inward lug having keypad engagement in said groove.

34. The combination of claim 32, wherein said handle has a longitudinal groove in longitudinally guiding location of said tie element.

35. The combination of claim 32, wherein said ring and said tie element are separate pieces having snap-lock engagement.

36. In combination with a surgical knife instrument, wherein an elongate handle mounts a surgical bladed implement at the end of a longitudinal stem which offsets the implement beyond an end of the handle, said bladed implement having a transverse section which has a maximum width that substantially exceeds the thickness of said section, a sheath of pliant material having a through passage which substantially conforms to said maximum-width section and which envelops the implement, said sheath having a blunt profile at its distal end, and said sheath having such frictional engagement with said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said stem extending in the longitudinal direction of and beyond said handle, and said implement being at angular offset with respect to said stem, said sheath enveloping at least the angularly offset portion of said implement and being sufficiently flexible to negotiate the juncture of said angular offset with said stem.

37. The combination of claim 36, in which the proximal end of said sheath is in guided conformance to said stem in at least the region of adjacency to said implement.

38. The combination of claim 36, in which the angularly offset elongate course of said implement is generally arcuate, and said sheath compliantly conforms to said course.

39. The combination of claim 38, in which the general arc of said course is in the direction of reducing angular deviation from the axis of said stem.

40. The combination of claim 29, in which said sheath comprises upper and lower panels of conforming contour, with registering longitudinal edges that are bonded to each other.

41. In combination with a surgical knife instrument, wherein an elongate handle mounts a surgical implement at the end of a longitudinal stem which offsets the implement beyond an end of the handle, a sheath of pliant material having a through passage which envelope the implement, said sheath having a blunt profile at its distal end, said sheath having such frictional engagement with said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said sheath comprising upper and lower panels of conforming contour and formed as a single blank with contiguous longitudinal edges which, when folded for registration of said panels, define one of the longitudinal edges of said sheath, the other longitudinal edges being in bonded registration with each other.

42. In combination with a surgical knife instrument, wherein an elongate handle mounts a surgical implement at the end of a longitudinal stem which offsets the implement beyond an end of the handle, a sheath of pliant material having a through passage which envelops the implement, said sheath having a blunt profile at its distal end, and said sheath having such frictional engagement with said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said sheath comprising upper and lower panels of conforming contour, with registering longitudinal edges that are bonded to each other, and one of said panels integrally including a tie element extending to a point of longitudinally guided location at said handle.

43. A phacoknife assembly, comprising an integrally formed sharpened blade at angular offset from an elongate stem, an elongate handle mounting said stem at one longitudinal end, the exposed length of said stem being at least the length of the bladed angular offset, and a sheath in circumferential overlap of said blade and compliantly engaged to said blade, said sheath being open at its distal end for actuated through-passage of said blade upon actuated retraction of said sheath, said sheath being reduced at its proximal end and in slidably guided relation to said stem, and a tie element connected to the proximal end of said sheath, said tie element extending to a location of longitudinally guided relation with said handle.

44. An insertion tool for use in intraocular-lens implantation in the capsular bag of an eye from which cataractous material has been removed, said tool comprising an elongate handle with a reduced elongate stem extending beyond an end of said handle, means at the distal end of said stem for releasably locating an intraocular lens unit having a circular lens and two diametrically opposed compliant haptics of generally J-configuration, and a sheath retractably carried by the distal end of said stem, said sheath being open at its longitudinal ends and longitudinally overlapping said lens unit with said haptics stressed inward by sheath confinement which clears the diametral span of said lens, and actuating means carried by said handle and connected to said sheath for selectively retracting said sheath in the course of positioning the lens unit in the capsulary bag.

45. The tool of claim 44, wherein the proximal end of said sheath is in reduced and slidably guided conformance with said stem.

46. The tool of claim 44, wherein said means at the distal end of said stem comprises bifurcated-arm formations spaced to loosely retain said lens in the span between bifurcated arms, said lens being frictionally retained in said space essentially only by the friction of stressed haptic confinement by said sheath.

47. The tool of claim 45, wherein said means at the distal end of said stem comprises a transverse groove for locating reception of part of the peripheral edge of said lens, said lens being frictionally retained and within said sheath essentially only by the friction of stressed haptic confinement by said sheath.

48. The tool of claim 44, wherein said elongate stem is bent to position said distal end at angular offset from the proximal end of said stem.

49. The tool of claim 48, wherein the angular offset of the distal end is along an elongate course which is generally arcuate.

50. A phacoknife assembly, comprising an integrally formed sharpened and pointed blade at angular offset from an elongate stem, an elongate handle mounting said stem at one longitudinal end, the exposed length of said stem being at least the length of the bladed angular offset, said blade having a transverse section which has a maximum width that substantially exceeds the thickness of said section, and a plastic sheath in circumferential overlap of said blade and compliantly engaged to said blade, said sheath being closed at its distal end for actuated knife-cutting passage of said blade through the closed distal end of said sheath upon actuated retraction of said sheath, and a rearwardly extending flexible retraction element connected to the proximal end of said sheath, whereby said retraction element provides means of remote retraction of said sheath and a knife-cutting passage of said blade through the closed distal end of said sheath.

51. The phacoknife assembly of claim 50, wherein said flexible retraction element extends to a location of longitudinally guided relation with said handle.

52. In combination, an elongate handle mounting a bladed surgical implement at the end of a longitudinal stem which longitudinally offsets the implement beyond an end of the handle, a sheath having a through passage which envelops the implement, actuating means accessible in the vicinity of said handle and connected to said sheath for selectively retracting said sheath from its position of enveloping the implement, and said sheath having opposed closely spaced relatively wide panels with such frictional engagement to opposite surfaces of the blade of said implement as to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said actuating means having longitudinally aligned and smoothly continuous connection to said sheath, and said connection being integrally formed with at least one of said panels.

53. In combination, an elongate handle mounting a bladed surgical implement at the end of a longitudinal stem which longitudinally offsets the implement beyond an end of the handle, a sheath having a through passage which envelops the implement, an elongate tie element connected to said sheath and extending to a point of longitudinally guided and frictional restraint location at said handle, and said sheath having opposed closely spaced relatively wide panels adjacent opposite surfaces of the blade of said implement, said frictional restraint being sufficient to permit sheathed-implement insertion along a surgically prepared tunnel, prior to retraction of said sheath to thereby expose said implement for its part in a surgical procedure wherein the operative use of said implement is to occur only after sheath-piloted insertional passage through at least a predetermined portion of the prepared tunnel, said elongate tie element having longitudinally aligned and smoothly continuous connection to said sheath, and said connection being integrally formed with at least one of said panels.

* * * * *